United States Patent [19]

Cooper et al.

[11] Patent Number: 4,966,154

[45] Date of Patent: Oct. 30, 1990

[54] MULTIPLE PARAMETER MONITORING SYSTEM FOR HOSPITAL PATIENTS

[75] Inventors: Jonni Cooper, P.O. Box 5333, Indian Rocks Beach, Fla. 33535; Tello Adams, Seminole, Fla.

[73] Assignee: Jonni Cooper, Indian Rocks Beach, Fla.

[21] Appl. No.: 152,272

[22] Filed: Feb. 4, 1988

[51] Int. Cl.$^5$ .......................................... A61B 5/0205
[52] U.S. Cl. ...................................... 128/671; 128/700
[58] Field of Search .............. 128/671, 723, 384, 385, 128/670, 644, 736, 700

[56] References Cited

U.S. PATENT DOCUMENTS

| 527,922 | 10/1894 | Backstrom et al. | 128/385 |
|---|---|---|---|
| 3,572,316 | 3/1971 | Vogelman et al. | 128/671 |
| 3,871,359 | 3/1975 | Pacela | 128/723 |
| 3,996,928 | 12/1976 | Marx | 128/671 |
| 4,090,504 | 5/1978 | Nathan | 128/670 |
| 4,122,843 | 10/1978 | Zdrojkowski | 128/644 |
| 4,129,125 | 12/1978 | Lester et al. | 128/671 |
| 4,202,212 | 5/1980 | Allen et al. | 128/719 |
| 4,356,825 | 11/1982 | Veth | 128/671 |
| 4,403,215 | 9/1983 | Hofmann et al. | 128/723 |
| 4,411,267 | 10/1983 | Heyman | 128/385 |
| 4,494,553 | 1/1985 | Sciarra et al. | 128/671 |
| 4,517,986 | 5/1985 | Bilgutay | 128/671 |
| 4,572,197 | 2/1986 | Moore et al. | 128/736 |
| 4,709,704 | 12/1987 | Lukasiewicz | 128/734 |

FOREIGN PATENT DOCUMENTS

| 0212278 | 3/1987 | European Pat. Off. | 128/670 |
|---|---|---|---|
| 3444635 | 6/1986 | Fed. Rep. of Germany | 128/671 |
| 2119241 | 12/1974 | France | 128/671 |

OTHER PUBLICATIONS

Marriott et al., "Constant Monitoring for Cardiac Dysrhythmias and Blocks," Modern Concepts of Cardiovascular Disease, vol. 39, No. 6, Jun. 1970.

Primary Examiner—Lee S. Cohen
Assistant Examiner—Kennedy J. Schaetzle

[57] ABSTRACT

A multiple parameter monitoring system for ambulatory human patients utilizes a separate harness to be removably worn by each patient. The harness is adapted to engage the chest of the patient and incorporates a first ECG data sensing device engaging the patient to produce first and second analog voltages having variable magnitudes which are measurements of the body MCL1 and MCL6 data respectively; a second respiratory amplitude sensing device to produce a first analog signal having a variable magnitude which is a measurement of the respiratory amplitude of the patient; and a third temperature sensing device engaging the patient to produce a second analog signal which is a measurement of the temperature of the patient.

19 Claims, 3 Drawing Sheets

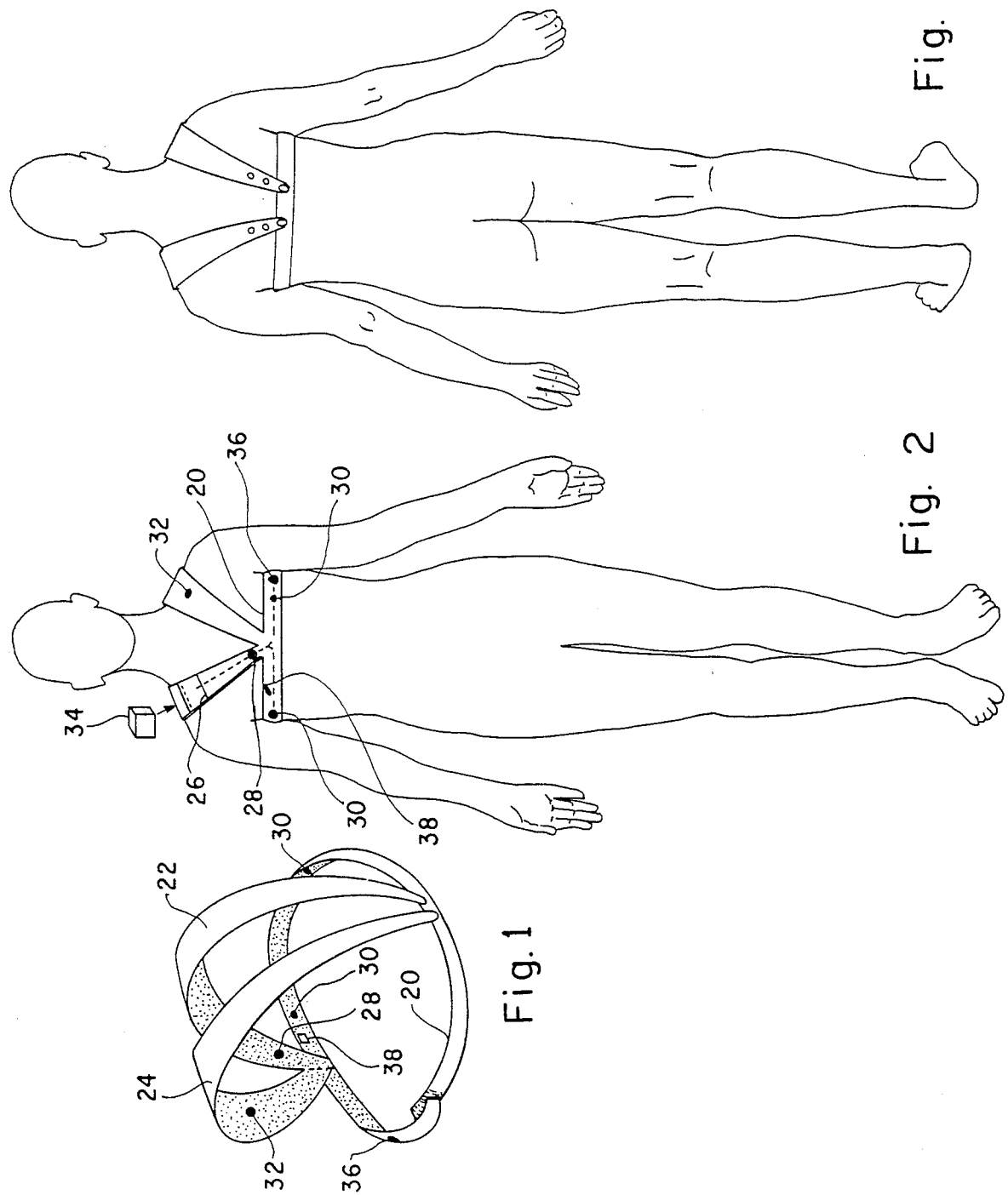

MULTIPLE PARAMETER MONITORING SYSTEM FOR HOSPITAL PATIENTS

BACKGROUND OF THE INVENTION

When a seriously ill patient enters a hospital, it is necessary to continuously check vital signs of the patient, as for example, ECG, heart rate, body temperature and respiratory data, because changes in such data which exceed specified maximum values or fall below specified minimum values may indicate that special corrective measures or treatments may be immediately necessary to safeguard the health or even the life of the patient.

While it is sometimes possible to have a skilled attendant accompany each such patient while the patient is ambulatory, the economics of medical car do not normally allow for such treatment. According, special equipment, known in the art as multiple parameter monitoring systems, have been developed wherein each patient is equipped with certain measuring and monitoring apparatus which transmits the necessary data to a central station staffed by nurses or other skilled attendants. The station is provided with other apparatus which receives and stores for print out any abnormal data transmitted. The receiving station contains high-low alarms which are activated automatically if changes in data exceed or fall below the specified maximum or minimum values.

Patients using current telemetry systems often find the apparatus to be heavy, akward to wear and uncomfortable to carry. Moreover, the known systems are expensive, difficult to install and maintain, and offer minimal data.

It is an object of the present invention to provide a new and improved multiple parameter monitoring system which offers complete vital signs [except BP] and the best two diagnostic leads of the ECG. This system is much less expensive, can monitor a large number of patients, and it can be istalled and maintained easily.

Another object is to provide a new and improved multiple parameter monitoring system which incorporates apparatus for use by patients which is light in weight, easy to use and comfortable to wear.

SUMMARY OF THE INVENTION

In accordance with the princiles of the invention, the apparatus to be used by patients takes the form of a separate harness to be worn by each patient. The harness, which can be easily fitted onto or removed from a patient, is adapted to encircle the chest of the wearer.

The harness is provided with or carries first ECG data sensing means, second respiratory sensing means and third temperature sensing means. Each of these means includes appropriate sensors and/or terminals which are automatically moved into engagement or contact with appropriate portions of the body when the harness is fitted onto the wearer.

The first means produces first and second analog voltages having variable magnitudes which are measurements of the MCL1 and MCL6 data respectively of the wearer. "MCL" is an abbreviation of the term "modified chest lead" which is used by physicians to identify the chest leads used in certain types of electrocardiographs. The numerals following the abbreviation identify the different locations on the chest at which the various leads are to be attached. It is known that the two most significant voltages obtained for use in producing electrocardiograms are obtained between the MCL1 and ground electrodes, referred to in the art as MCL1 data, and between MCL6 and ground electrodes, referred to in the art as MCL6 data.

The second means produces a first analog signal having a variable magnitude which is a measurement of the respiratory amplitude of the wearer.

The third means produces a second analog signal which is a measurement of the temperature of the wearer.

An electronic module is securable to the harness and is adapted to be carried therewith or therein. The module incorporates various means to carry out a variety of functions. It responds to the first analog signal to derive therefrom a third analog voltage having a variable magnitude which is proportional to the respiratory amplitude. It responds to the second analog signal to derive therefrom a fourth analog voltage having a variable magnitude which is proportional to the temperature.

Thereafter, the first, second, third and fourth voltages are sampled. The first and second voltages are sampled at a first fixed rate; the third voltage is sampled at a second and lower fixed rate; and the fourth voltage is sampled at a third and still lower fixed rate. The timing of the sampling operation is so controlled that only one voltage is sampled at a time.

As will be explained in more detail in a following section of this application, it is highly advantageous to use these different sampling rates rather than use only one rate, which would then have to be the highest of these three rates. The use of these three rates is permitted because of the relationships between the various parameters measured. The ECG data changes relatively rapidly, and thus needs a relatively high sampling rate. The respiratory data changes less rapidly and thus can be sampled at a lower sampling rate. The temperature data changes even less rapidly and thus can be sampled at a still lower sampling rate.

The sampled values are then converted into corresponding digital equivalents and are multiplexed and encoded into a single signal. This signal is used to frequency modulate a carrier wave of selected frequency. The modulated wave is then transmitted.

A monitoring station is disposed remotely from the patients. The patients can be ambulatory or can remain in their rooms, either in bed or sitting in chairs, since the transmission is not affected as long as the harnesses are worn. The transmitted wave is received at the station and is demodulated to extract the serial signal. The serial signal is then converted into the individual parallel equivalents. These equivalents are then processed by a computer.

Each of the original sensed voltages and signals has preselected maximum and minimum parameters such as magnitudes, rates, waveshapes and the like. When any one of these voltages or signals exceeds its preselected maximum value or falls below its preselected minimum value, an appropriate alarm signal is activated by the computer. If desired, under computer control, the abnormal data can be stored for print out and the vital signs of each patient in turn can be displayed on a video monitor.

All of the foregoing as well as additional objects and advantages of the invention will either be explained or will become obvious to those in the art when this specification is studied in conjunction with the accompanying drawings.

BRIEF DESCRIPTION OF THE DRAWINGS

FIG. 1 is a perspective view of the harness.

FIG. 2 is a front view of a patient showing the harness in position.

FIG. 3 is a rear view of a patient showing the harness in position.

DETAILED DESCRIPTION OF PREFERRED EMBODIMENTS

Figure 4:
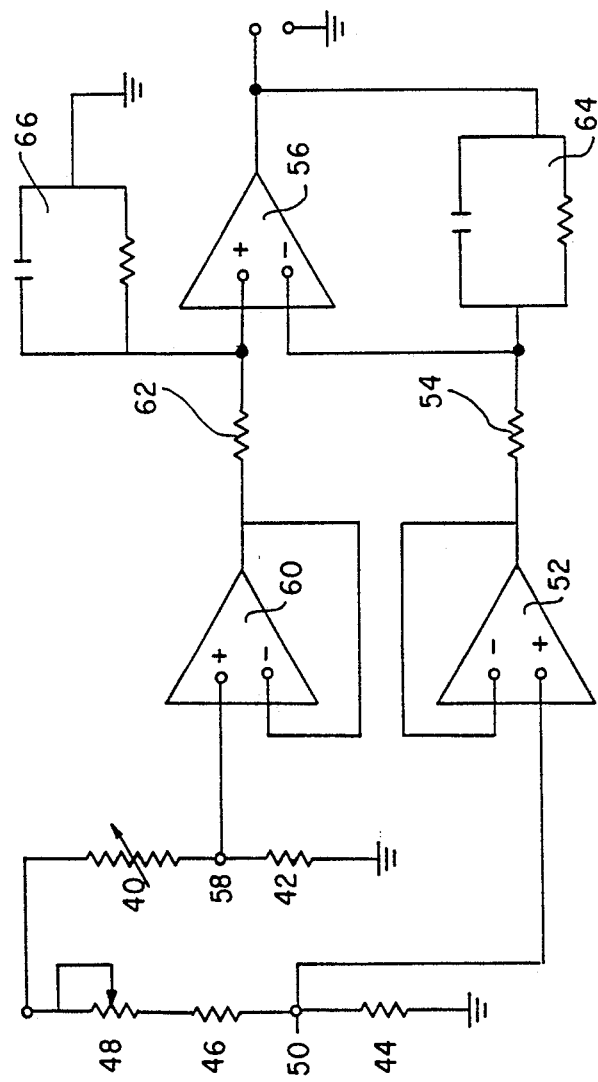
FIG. 4 is a circuit diagram of an impedance to voltage converter utilized in the electronic module of FIG. 5.

Referring first to FIGS. 1–3, a flexible harness made of cloth, leather, plastic or other suitable material employs a horizontal belt 20 which detachably encircles the chest of a patient and is adjustable in length. First and second shoulder straps 22 and 24 are joined together to the belt at the front of the patient. Each strap then extends over a corresponding shoulder and is connected to the belt at the rear of the patient. The straps are each individually adjustable in length.

Strap 22 carries an MCL1 electrode 28 at the front of the patient adjacent the belt 20 and is also provided with a pouch 26 in which a battery powered electronic module 34 can be removably disposed. The belt carries at the front of the patient in spaced position respiratory electrodes 30, a temperature sensor 38 and an MCL6 electrode 36. Strap 24 carries a reference electrode 32.

Respiratory data is obtained by measuring the change in impedance between the two respiratory electrodes 30. It is necessary to convert the changes in impedance into changes in voltage before the data can be further processed. To this end, an impedance to voltage converter is employed as shown in FIG. 4. The respiratory impedance 40 as it appears between electrodes 30 is disposed in a bridge with additional resistances 42, 44 and 46 and potentiometer 48. The junction 50 of resistances 44 and 46 is connected through operational amplifier 52 and an additional resistance 54 to one input of a second operational amplifier 56. The junction 58 of resistances 40 and 42 is connected through operational amplifier 60 and an additional resistance 62 to the other input of amplifier 56. Resistances 42 and 44 are equal; resistances 54 and 62 are equal and parallel resistance-capacitance networks 64 and 66 are identical. Network 64 is connected between the one input to amplier 56 and its output terminal. Network 66 is connected between the other input to amplifier and ground. The desired output voltage appears between the output terminal of amplifier 56 and ground. The networks are low pass noise filters. In use, the converter is first calibrated by using a known respiratory resistance and adjusting the potentiometer 48 until the sum of the potentiometer resistance and resistance 46 is equal to the known respiratory resistance, whereby the voltage difference between junctions 50 and 58 is zero.

Figure 5:
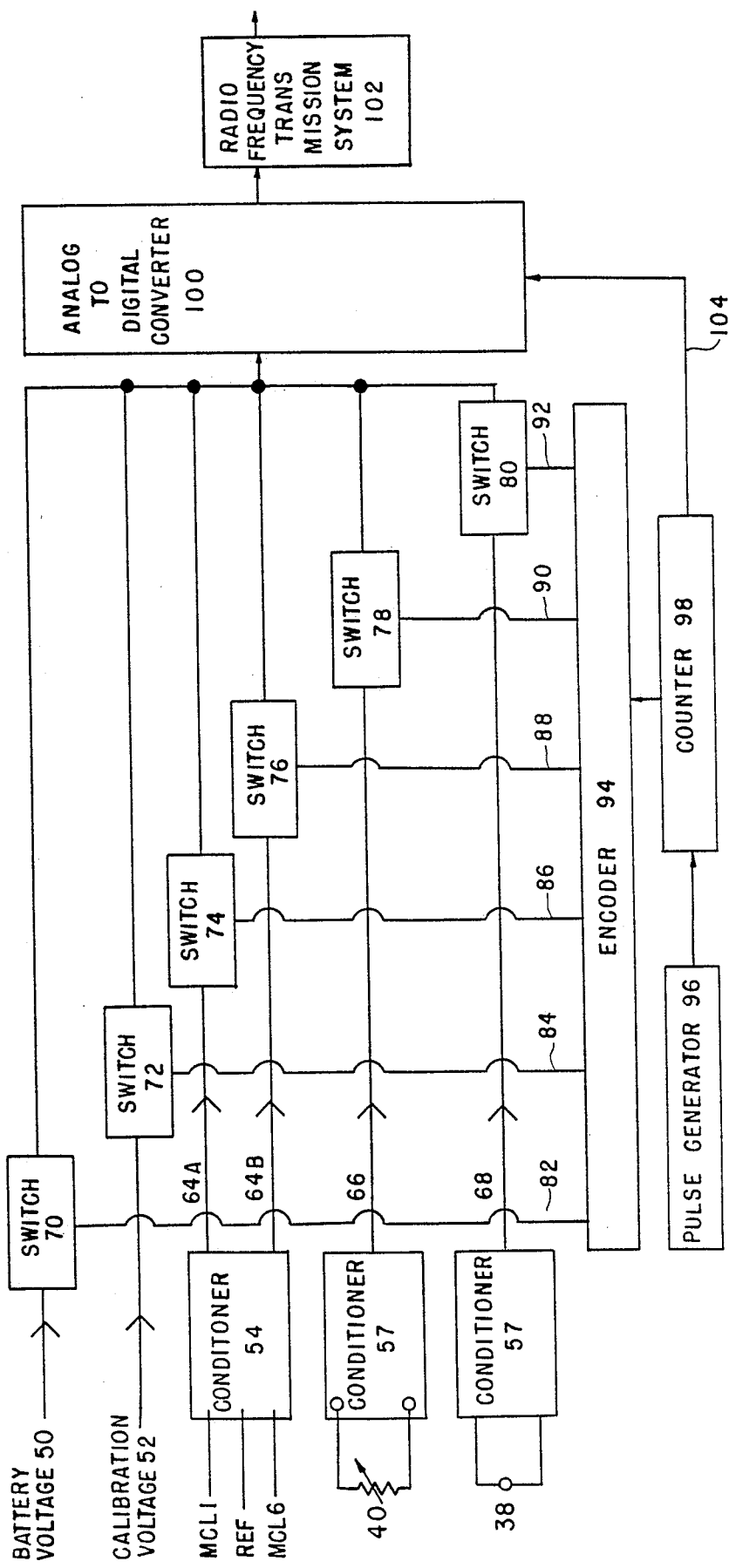
FIG. 5 is a block diagram of an electronic module used by each patient.

As shown in FIG. 5, the electronic module utilizes battery voltage 50 and calibration voltage 52. The ECG voltages are supplied to signal conditioner 54, which normalizes these voltages and causes them to fall into a standard voltage range as output voltages 64A and 64B respectively. Signal conditioner 57 which, unlike conditioner 54 which responds directly to input voltages, includes the converter of FIG. 4 as an initial stage and the conditioner of 54 as a final and following stage, receives at its input the respiratory impedance, and produces a normalized output voltage 66. The body temperature sensor can be a temperature sensitive rectifier or RTD, in which case the sensor acts as a variable impedance and is connected to a second like conditioner 57 which produces a normalized output voltage 68.

All these voltages are to be multiplexed. Each of voltages 50, 52, 64A, 64B, 66 and 68 are supplied as an input to a corresponding one of switches 70, 72, 74, 76, 78 and 80. These switches are opened and closed in sequence to sample the various voltages. Each switch is controlled by being connected by a corresponding one of control leads 82, 84, 86, 88, 90 and 92 to the output of encoder 94. Encoder 94 is controlled by input pulses supplied from a clock generator 96 which supplies regularly spaced pulses to the input of counter 98. Counter 98 supplies appropriately timed signals to the encoder which then operates the switches.

The two ECG signals are sampled at the highest frequency, for example at one hundred and sixty times per second via switches 74 and 76. The respiratory channel is sampled at a tenth of the sampling frequency of the ECG signals via switch 78. The body temperature, battery voltage and calibration voltage all vary at a much slower rate and can be sampled at a common still lower frequency, as for example at one tenth of the sampling frequency used with the respiratory channel, via switches 70, 72 and 80.

The switches together constitute a single multiplexer and only one switch can be closed at any one time. The outputs of the switches are connected to the input of an analog to digital converter 100. The output of the converter is supplied to the input of a known type of radio frequency transmission system 102, for example a serial PCM FM system which transmits the composite signal to a receiver system in the remote central unit.

Since the signal format is fixed, each data channel appearing in the same time position in each frame, the beginning of each frame [or sub frames if used] is defined by causing the encoder to produce a unique pattern, such as all zeros at the appropriate places in the bit stream. A strobe signal can also be generated in the encoder at every sample time and supplied via lead 104 to the converter to control the conversion operation.

Figure 6:
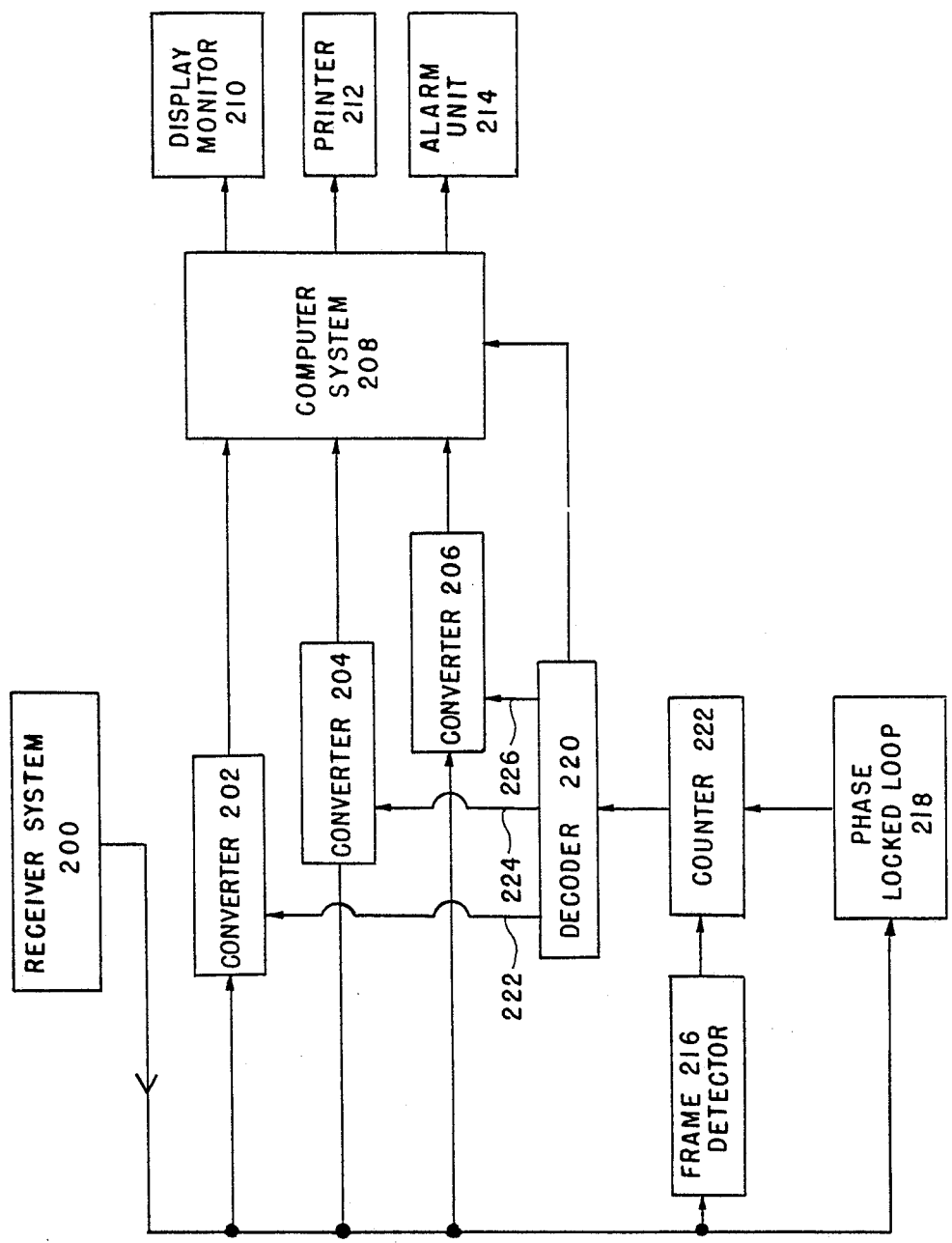
FIG. 6 is a block diagram of the remote central unit.

Refering now to FIG. 6, the composite radio frequency signal from the transmission system 102 is received by a known radio frequency receiver system 200 in the remote central unit. The receiver system processes the received signal is known manner to reproduce the digital signals in serial form appearing at the output of the converter 100 of FIG. 5. These signals are supplied in parallel to first, second and third serial to parallel converters 202, 204, and 206 which supply the digital output signals representing, for converter 202, the ECG data obtained from conditioner 54, for converter 204, the repiratory data from conditioner 57, and for converter 206, the body temperature data from conditioner 57 as well as the battery voltage data and the calibration voltage data. While each converter receives all signals, the converters are so controlled that only the proper signals are processed by each converter.

The outputs from the converters are supplied to a computer system 208, which stores the data, makes the requisite calculations and feeds the information to a display monitor 210, a printer 212 and an alarm unit 214. Unit 214 produces the required alarm signals previous referred to. Since each patient is assigned a separate transmission channel, and the individual transmitter systems are appropriately coded and timed, the receiver receives only one channel at a time, and the display, print-out and alarms are appropriately timed and identified by the computer.

In order to operate the converters, the signal yielded by system 200 is also supplied to the input of a frame detector 216 and a phase locked loop 218. The outputs from detector 216 and loop 218 are supplied to the input of a counter 222. The counter output is connected to the input of a decoder 220. The outputs 222, 224 and 226 of the decoder are connected to converters 202, 204 and 206 to control the demultiplexing operation accordingly.

While the invention has been described with particular reference to the drawings and specific preferred embodiments, the protection sought is to be limited only by the terms of the claims which follow.

What is claimed is:

1. Apparatus adapted for use in a multiple parameter monitoring system for ambulatory human patients, said apparatus comprising:
    a separate harness to be removably worn by each patient, said harness being adapted to engage the chest of the patient and incorporating
    first ECG data sensing means for engaging the patient to produce first and second analog voltages having variable magnitudes which are measurements of the body MCL 1 and MCL 6 data respectively, said first means including MCL 1 and MCL 6 electrodes and a ground electrode, the first analog voltage appearing between the MCL 1 and ground electrodes, the second analog voltage appearing between the MCL 6 and ground electrodes;
    second respiratory sensing means for engaging the patient to produce a first analog signal having a variable magnitude which is a measurement of the respiratory amplitude of the patient, said second means including two additional spaced electrodes for engaging the patient and exhibiting a respiratory impedance therebetween; and
    third temperature sensing means for engaging the patient to produce a second analog signal which is a measurement of the temperature of the patient, said third means including a temperature responsive impedance element.

2. The apparatus of claim 1, further including an electronic module securable to the harness and provided with fourth means responsive to the first analog signal to produce a third analog voltage having a variable magnitude which is proportional to the respiratory resistance, said fourth means including an impedance to voltage converter.

3. The apparatus of claim 2, wherein the module includes fifth means responsive to the second analog signal to produce a fourth analog voltage having a variable magnitude which is proportional to the temperature, said fifth means including another impedance to voltage converter.

4. The apparatus of claim 3, further including signal conditioners, wherein the first, second, third and fourth analog voltages are normalized by said signal conditioners.

5. The apparatus of claim 4, wherein the module includes sixth means responsive to the first, second, third and fourth analog voltages to obtain sampled values thereof, the first and second voltages being sampled at a first fixed rate, the third voltage being sampled at a second and lower fixed rate, and the fourth voltage being sampled at a third and still lower fixed rate, the timing of the sampling operation being so controlled that only one voltage is sampled at a time.

6. The apparatus of claim 5, wherein the module includes seventh means responsive to the sixth means to convert the sampled voltages to digital equivalents and thereafter to multiplex these equivalents as a serial signal.

7. The apparatus of claim 6, wherein the module includes a transmitter system for producing a carrier wave of selected frequency, the system including eighth means responsive to the seventh means to frequency modulate said carrier wave with the multiplexed serial signal and to transmit the frequency modulated wave.

8. The apparatus of claim 7, further including a monitoring station spaced apart from all mobile patients and including ninth means responsive to the eighth means to receive the transmitted wave.

9. The apparatus of claim 8, wherein the station includes tenth means responsive to the ninth means to demodulate the wave and extract the series signal therefrom.

10. The apparatus of claim 9, wherein the station includes eleventh means responsive to the tenth means to convert the series signal into the individual parallel digital equivalents.

11. The apparatus of claim 10, wherein the station includes a computer responsive to the digital equivalents to cause the first and second analog voltages and first and second analog signals to be displayed visually.

12. The apparatus of claim 11, wherein each of the first and second analog voltages and first and second analog signals has preselected maximum and minimum parameter limits and wherein the station includes an alarm device controlled by the computer to produce an alarm signal whenever any of the analog voltages and signals falls below the preselected minimum parameter limits or exceeds the preselected maximum parameter limits.

13. The apparatus of claim 1, wherein the harness includes a belt encircling the chest of the patient and having front and rear sections, a first strap extending over one shoulder of the patient and connected between the front and rear sections, and a second strap extending over the other shoulder of the patient and connected between the front and rear sections.

14. The apparatus of claim 13, wherein the first and second straps are joined at the front section of the belt and are separated at the rear section of the belt.

15. The apparatus of claim 14, wherein the second means is disposed in the belt.

16. The apparatus of claim 15, wherein the third means is disposed in the belt.

17. The apparatus of claim 16, wherein the first means is disposed in the belt and straps.

18. The apparatus of claim 17, wherein the first means includes a reference electrode in one strap, an MCL1 electrode in the other strap, and an MCL6 electrode in the belt.

19. The apparatus of claim 18, wherein one of the straps contains a pouch adapted to receive removably an electronic module.

* * * * *